(12) United States Patent
Otto

(10) Patent No.: US 7,083,955 B2
(45) Date of Patent: Aug. 1, 2006

(54) PREPARATION OF LACTIC ACID FROM A PENTOSE-CONTAINING SUBSTRATE

(75) Inventor: Roel Otto, Gorichem (NL)

(73) Assignee: Purac Biochem BV, Gorichem (NL)

( * ) Notice: Subject to any disclaimer, the term of this patent is extended or adjusted under 35 U.S.C. 154(b) by 0 days.

(21) Appl. No.: 10/755,392

(22) Filed: Jan. 13, 2004

(65) Prior Publication Data

US 2004/0203122 A1 Oct. 14, 2004

Related U.S. Application Data

(60) Provisional application No. 60/439,469, filed on Jan. 13, 2003.

(51) Int. Cl.
  *C12P 7/56* (2006.01)
  *C12P 17/00* (2006.01)
  *C12N 1/20* (2006.01)
  *A01N 63/00* (2006.01)

(52) U.S. Cl. .................. 435/139; 435/252.5; 435/117; 424/93.46

(58) Field of Classification Search ................ 435/139, 435/135, 252.31
  See application file for complete search history.

(56) References Cited

U.S. PATENT DOCUMENTS 4,110,477 A * 8/1978 Naruse et al. ................ 426/46
4,702,922 A * 10/1987 Wiesenberger et al. ....... 426/51
5,002,881 A * 3/1991 Van Nispen et al. ........ 435/139
6,022,537 A 2/2000 Combet-Blanc et al.

FOREIGN PATENT DOCUMENTS

WO   WO 97/13842 A   4/1997
WO   WO 03/008601 A2 *   1/2003

OTHER PUBLICATIONS

Godshell et al., 2002. Effect of macromolecules on sugar processing: comparison of cane and beet macromolecules. AVH Association 9th symposium, p. 23-30.*
Meyer GA. 1910. Zeitschrift des Vereines der Deutschen Zucker-Industrie 59: 1019-1020. Abstract Only.*
Pellet H. 1917. Annales de Chimie Analytique et Revue de Chimie Analytique Reunies 22: 43-47. Abstract Only.*
Low NH. 1997. Using GC to detect food adulteration. Agilent Technologies online article; http://www.chem.agilent.com/cag/peak/peak2-97/article1.html accessed Oct. 3, 2005. 3 pages.*
Sabinsa Corp. 2000. Lactospore. http://www.lactospore.com/back2.htm accessed Oct. 4, 2005. 5 pages.*
Payot et al. "Lactic Acid Production by *Bacillus Coagulans*—Kinetic Studies and Optimization of Culture Medium for Batch and Continuous Fermentations," Enzyme and Microbial Technology, vol. 24, 1999, pp. 191-199.

* cited by examiner

*Primary Examiner*—Irene Marx
*Assistant Examiner*—Lora E Barnhart
(74) *Attorney, Agent, or Firm*—Oliff & Berridge PLC

(57) ABSTRACT

Cost-effective processes for producing lactic acid and/or lactate from pentose-containing substrates, such as xylose-containing substrates, are provided. In particular, processes for producing lactic acid and/or lactate include fermentation of pentoses, such as xyloses, to enantiomerically pure lactic acid and/or lactate by moderately thermophilic *Bacillus* species. This fermentation runs by a homofermentive pathway and produces predominantly $C_3$ compounds, so that $C_3$ compounds can be recovered as lactic acid and/or lactate.

9 Claims, No Drawings

PREPARATION OF LACTIC ACID FROM A PENTOSE-CONTAINING SUBSTRATE

This nonprovisional application claims the benefit of U.S. Provisional Application No. 60/439,469, filed Jan. 13, 2003.

FIELD OF THE INVENTION

This invention relates to the production of lactic acid from pentose-containing substrate, particularly from xylose-containing substrate.

BACKGROUND OF THE INVENTION

Lactic acid, and its salts known as lactate, are commercially viable products useful in various fields including medicine, biodegradable polymers and food processing. Currently, lactic acid is commercially produced from glucose, starch, liquefied starch or sucrose. At present, these substrates are an important contributor to the manufacturing cost price of lactic acid. Lignocellulosic biomass offers a cost attractive alternative as a substrate for the biological production of lactic acid because it is readily available, has no competing food value, and is less expensive than either starch or sucrose. Theoretically, a microorganism would be able to ferment the sugars contained in the biomass to lactic acid. However, several obstacles preclude efficient utilization of this feedstock by a microorganism for lactic acid production. Lignocellulosic substrates are largely composed of cellulose, hemicellulose and lignin. While several microorganisms can efficiently ferment the glucose component in cellulose, conversion of the pentose sugars contained in the hemicellusose fraction of biomass has proven more difficult. The most abundant pentose sugars in hemicellulose include D-xylose and L-arabinose. Fermentation of xylose and arabinose remains a major obstacle for economical conversion of plant-originated biomass.

Many heterolactic and facultative heterolactic lactic acid bacteria are able to ferment pentoses. The metabolic route used by these organisms to ferment these sugars is simple: a pentose e.g. D-xylose (aldose) enters the cell where it is isomerised to xylulose (ketose) and subsequently phosphorylated at the cost of 1 ATP to yield xylulose-5-phosphate, which is then cleaved into glyceraldehyde-3-phosphate and acetyl-phosphate by phosphoketolase (EC 4.1.2.9). This metabolic pathway is known as the phosphoketolase pathway (Lengeler, J. W.; G. Drews; H. G. Schlegel, *Biology of prokaryotes*, 1999, Thieme Verlag, Stuttgart, Germany). The glyceraldehyde-3-phosphate that is produced in the phosphoketolase reaction is converted to pyruvic acid as in the Emden-Meyerhof pathway yielding 2 ATP and 1 $NADH_2$ (Lengeler, J. W.; G. Drews; H. G. Schlegel, *Biology of prokaryotes*, 1999, Thieme Verlag, Stuttgart, Germany) Pyruvic acid is finally reduced with $NADH_2$ to lactic acid. The acetyl-phosphate that is produced in the phosphoketolase reaction is converted by acetate kinase (EC 2.7.2. 1) to acetate with the formation of 1 ATP. In the course of the fermentation of a pentose, 1 $NADH_2$ is formed and consumed; the net ATP yield is 2 per mol pentose. Heterofermentative lactic acid bacteria use a similar pathway for the fermentation of hexoses. A hexose e.g. glucose is first phosphorylated to glucose-6-phosphate, oxidised to yield 6-phosphogluconate and finally oxidatively decarboxylated to yield ribulose-5-phosphate and carbon dioxide. Epimerisation of ribulose-5-phosphate yields xylulose-5-phosphate, which enters the phosphoketolase pathway. Contrary to the fermentation of pentoses the fermentation of hexoses by heterofermentative lactic acid bacteria produces an excess of reducing power (3 $NADH_2$) which is used to reduce acetyl-phosphate to ethanol and pyruvic acid to lactic acid. In this scheme no acetic acid is produced from acetyl-phosphate, hence the ATP yield of the fermentation of hexoses is only half that of the fermentation of pentoses; 1 ATP per mol hexose fermented. In the above metabolic pathway of pentose fermentation the enzyme phosphoketolase plays a fate-determining role because it is this enzyme that breaks up the $C_5$ carbon skeleton of pentoses into a $C_3$ moiety, which finally can be recovered as lactic acid and a $C_2$ moiety, which ends up as acetic acid. For the production of lactic acid, which understandably is geared towards maximal lactate yield the formation of acetic acid is wasteful. A small number of reports, however, indicate that some *Lactobacillus* species e.g. *Lactobacillus* species MONT4 ferment certain pentoses almost exclusively to lactic acid (Barre P., *Identification of thermobacteria and homofermentative, thermophilic pentose utilizing Lactobacilli from high temperature fermenting grape must*, J. Appl. Bacteriol. 1978, 44, 125–129). In *Lactobacillus* species MONT4, pentoses are dissimilated by a pathway, which does not involve phosphoketolase, but by a metabolic pathway that involves transaldolase (EC 2.2.1.2) and transketolase (EC 2.2.1.1) (U.S. Pat. No. 5,798,237). This pathway is known as the transaldolase/transketolase pathway.

The higher lactate yield on pentoses of this pathway, however, comes at a price for the organism. Whilst the ATP yield of the phosphoketolase pathway is 2 per mol of pentose that of the transaldolase/transketolase pathway is 5 ATP per 3 moles of pentose. This lower ATP yield may be one of the reasons why lactic acid bacteria with a homolactic pattern of pentose fermentation are relatively rare. From an industrial point of view it is relevant to note here that *Lactobacillus* species MONT4 is unable to ferment xylose. Recently *Lactobacillus* species MONT4, was genetically engineered with xylose isomerase and xylulokinase genes from *Lactobacillus pentosus* to impart to this organism the ability to ferment xylose. This has been described in U.S. Pat. No. 5,798,237.

Although micro organisms such as *Lactobacillus* species are producers of lactic acid, certain properties make these organisms less suitable for the industrial manufacture of lactic acid: *Lactobacillus* species require a fair amount of organic nitrogen in the fermentation medium, as well as growth promoting substances, so that the broth becomes more expensive and the lactic acid more difficult to purify when a simple fementation medium can be used. Furthermore many *Lactobacillus* species, *Lactobacillus* sp MONT4 included produce lactic acid with a low enantiomeric purity (see: Barre, P. *Identification of thermobacteria and homofermentative, thermophilic pentose utilizing Lactobacilli from high temperature fermenting grape must.* J. Appl. Bacteriol. 1978, 44, 125–129). It is one of the objects of this invention to provide a method, which is devoid of these disadvantages.

We have now found that some naturally occurring moderately thermophilic *Bacillus* species are able to ferment pentoses, more specifically xylose, anearobically, predominantly to enantiomerically pure lactic acid and/or lactate. Said conversion of pentoses leads to virtually only $C_3$ compounds, i.e. said conversion runs via a homofermentative route, which $C_3$ compounds can be recovered as lactic acid and/or lactate. Moderately thermophilic *Bacillus* species are bacterial strains which are capable of growing at temperatures between 30–65° C. It is further of importance that said fermentation is conducted anaerobically. In the case of anaerobic fermentation, the process can be easily carried out in industrial scale, because no oxygen supply is needed by e.g. extensive stirring equipment. Examples hereof are *Bacillus coagulans* and *Bacillus smithii* and genetically modified lactic acid-producing species thereof. These types of microorganisms are nutritionally less demanding than *Lactobacilli*. An additional advantage of these types of microorganisms, is that the higher growth temperatures (*Lactobacillus* species have growing temperatures of at most 50° C.) make it easier to avoid infections in industrial scale fermentation systems. Hence, the present invention is directed to a process for the preparation of lactic acid wherein a pentose-containing substrate is homolactically fermented by a moderately thermophilic *Bacillus* species, which ferments anaerobically.

The choice of substrates will depend on cost and supply of the substrate to be fermented to lactic acid and/or lactate. A typical low-cost supply of pentoses is from hemicellulose. Xylose, arabinose and other pentoses are liberated from hemicellulosic materials by treatment with steam and/or an acid or alkali. Smaller amounts of other sugars such as glucose are also separated during this treatment and are also fermented by the moderately thermophilic *Bacillus* species to lactic acid and/or lactate.

Lignocellulosic substrates comprise both cellulose, hemicellulose and lignine. These types of substrates may be made accessible for hydrolyzation by steam and/or mild acid or alkali treatment. When the substrate comprises cellulosic material, the cellulose may be hydrolyzed to sugars simultaneously or separately and also fermented to lactic acid. Since hemicellulose is generally easier to hydrolyze to sugars than cellulose, it is preferable to first prehydrolyze the hemicellulosic material, separate the soluble pentose sugars and then hydrolyze the cellulose. Hydrolyzation may be done enzymatically. (with cellulase for celluloses and hemicellulase for hemicellulose) or chemically by acid treatment. Both pentose and hexose sugars may be simultaneously or separately fermented to lactic acid and/or lactate using the moderately thermophilic *Bacillus* species. If so desired, the hexoses may be fermented by a different microorganism to lactic acid and/or lactate i.e. in mixed culture with e.g. yeasts, fungi or other known lactic acid-producing bacteria such as *Lactobacillus* species and *Bacillus* species differing from the ones used for the pentose fermentation.

The fermentation conditions to form lactic acid and/or lactate are known per se and are described in WO 01/27064, WO 99/19290, and WO 98/15517. Accordingly, the temperature may range from 0 to 80° C., while the pH (which decreases upon lactic acid formation) ranges from 3 to 8. A pH below 5 is generally desirable, as part of the lactic acid formed will then be present in its free-acid form instead of in its salt form. Furthermore, at low pH there is less risk of contamination with other micro organisms. Any of the many known types of apparatus may be used for the fermentation according to the present invention.

The microorganism according to the present invention may be used as a biologically pure culture or it may be used with other lactic acid producing microorganisms in mixed culture. Biologically pure cultures are generally easier to optimize but mixed cultures may be able to utilize additional substrates. One may also add enzyme(s) to the fermentation vessel to aid in the degradation of substrates or to enhance lactic acid production. For example, cellulase may be added to degrade cellulose to glucose simultaneously with the fermentation of glucose to lactic acid by microorganisms. Likewise, a hemicellulase may be added to degrade hemicellulose. As mentioned-above, said hydrolyzation (optionally by means of enzymes) may also be conducted prior to fermentation.

The moderately thermophilic *Bacillus* species-containing fermentation broth cultures are-relatively resistant to contamination by other microorganisms. Nonetheless, it is preferred to eliminate or disable pre-existing deleterious microorganisms in the substrate added to the moderately thermophilic *Bacillus* species. This may be done by conventional techniques like filtration, pasteurization and sterilization.

The moderately thermophilic *bacillus* species used in the process according to the invention may be grown both in so-called chemically defined media and in culture media which contain undefined compounds such as yeast extracts, peptone, tryptone, other meat extracts and complex nitrogen sources. The use of a chemically defined medium is preferred because it results in lactic acid and/or lactate with less impurities.

After fermentation, the lactic acid and/or lactate is separated from the fermentation broth by any of the many conventional techniques known to separate lactic acid and/or lactate from aqueous solutions. Particles of substrate or microorganisms (the biomass) may be removed before separation to enhance separation efficiency said separation may be conducted by means of centrifuging, filtration, flocculation, flotation or membrane filtration. This is for instance known from WO 01/38283 wherein a continuous process for the preparation of lactic acid by means of fermentation is described.

While the discussion of the fermentation in this specification generally refers to a batch process, parts or all of the entire process may be performed continuously. To retain the microorganisms in the fermentor, one may separate solid particles from the fermentation fluids. Alternatively, the microorganisms may be immobilized for retention in the fermentor or to provide easier separation.

After separation of the lactic acid and/or lactate from the fermentation broth, the product may be subjected to one or more purification steps such as extraction, distillation, crystallization, filtration, treatment with activated carbon etcetera. The various residual streams may be recycled, optionally after-treatment, to the fermentation vessel or to any previously performed purification step.

The present invention is further illustrated by the following examples, which are not to be construed as being limitative.

EXAMPLE 1

Lactic Acid Formation from Pentose Sugars by Moderately Thermophilic *Bacillus* Species Materials and Methods Media The yeast extract medium for growth of *Bacillus smithii* DSM 459 and 460 (DSM strains obtained from the German culture collection) contained per liter: 3.5 g DAS (diammonium sulfate), 2 g DAP (diammonium phosphate), 10 g yeast extract and buffered by 10 g BIS-TRIS (bis[2-hydroxymethyl]iminotris[hydroxymethyl]methane). Medium was autoclaved before use. D-ribose, D-xylose, D-arabinose or glucose was used as carbon source in a final concentration of 3%. Carbon sources were filter sterilized and added separately. The pH of the medium was adjusted to 6.6–6.7 with HCl. Yeast extract medium for growth of *Bacillus*

*coagulans* DSM 2314 was as described for *B. smithii* however containing 1 g/l yeast extract in stead of 10 g/l.

The minimal medium for growth of *B. smithii* DSM 2319 and *B. coagulans* DSM 2314 contained per liter: 2 g DAP, 3.5 g DAS, 10 g BIS-TRIS, 0.5 g KCl and 15 mg $MgCl_2$. The pH of the medium was adjusted to pH 6.8 with HCl. Medium was autoclaved before use. D-ribose, D-xylose, D-arabinose or glucose was used as carbon source in a final concentration of 3%. Carbon sources, growth factors and trace elements were filter sterilized and added separately. Final concentrations were: 0.024 mg/l biotine, 0.012 mg/l thiamine, 0.02 g/l methionine, 0.05 g/l yeast extract, 100 μl trace elements, 1 g/l $CaCl_2$. Trace elements contained per 100 ml: 0.36 g $FeCl_3$, 0.3 g $MnCl_2$, 0.24 g $CoCl_2$, 0.12 $ZnCl_2$.

Growth Conditions for Lactic Acid Production

All bacteria were plated from −80 glycerol stocks on yeast extract medium using glucose (5% w/w) as carbon source containing 10 g/l GELRITE (gellan gum, Sigma). Plates were incubated at 46° C. for 24–48 hours in anaerobic jars. Thereafter anaerobic cultures were prepared on yeast extract medium with glucose as carbon source (3% w/w) in sterile 10 ml tubes. The cultures were incubated at 54° C. for 24 hours. Thereafter 2% of the culture was transferred to tubes containing minimal medium with glucose, xylose, ribose or arabinose as carbon source. Tubes were incubated at 54° C. for 48 hours. After a second transfer (2%) to fresh medium and incubation at 54° C. for 48 hours, samples were taken for determination of biomass, pH and organic acid production. To determine biomass production, optical density at 610 nm was measured in a spectrophotometer against demineralised water. As an indication for (lactic) acid production, pH was measured in the cell broth. Thereafter cells were harvested by centrifugation (10 min, 8000 rpm), supernatant was filtered through 0.45 μm filters and kept at 4° C. for further analysis.

Analysis of Organic Acids, Ethanol and Sugars

Organic acids (lactic acid, acetic acid, formic acid, succinic acid) and ethanol were measured using derivatization and GLC.

Optical purity of lactic acid was measured by GLC. D- and L-Lactates were methylated to methyl-lactate and measured by headspace analysis on a chiral column.

Pentose sugars were analyzed with a DIONEX type DX 500 containing a CARBOPAC PA-1 column and a PAD (Pulsed Amperometric Detection type ED 40) detector using a flow of 1.0 ml/min.

RESULTS

*B. smithii* and *B. coagulans* were grown anaerobic at 54° C. on yeast extract and minimal medium containing 3% (w/w) arabinose, ribose or xylose (Table 1, Table 2). All strains performed a homolactic fermentation of pentose sugars producing mainly L-lactic acid. No detectable levels of acetic acid were found. Optical purity of the L-lactic acid produced was 96.7–99.7%. Other organic acids (formic, succinic) and ethanol were below detection level of 0.05% w/w in all cases. Analysis of residual sugars showed a decrease in xylose, ribose and arabinose concentrations depending on the carbon source used (data not shown).

TABLE 1

Acid production by thermophilic *Bacillus* species from pentose sugars in yeast extract medium at 54° C. after two transfers.

| Organism | C-source (3% w/w) | Lactic acid (% w/w) 48 h | Acetic acid[1] (% w/w) 48 h | Chiral purity L(+) lactate (S/R + S) * 100% 48 h | PH 48 h | OD 610 48 h |
|---|---|---|---|---|---|---|
| *B. coagulans* DSM 2314 | Xylose | 0.24 | n.d.[2] | 99.7 | 5.4 | — |
|  | Arabinose | 0.23 | n.d.[2] | 99.7 | 5.3 | — |
| *B. smithii* DSM 459 | Xylose | 0.39 | n.d.[2] | 98.9 | 4.1 | 0.9 |
|  | Arabinose | 0.24 | n.d.[2] | 99.1 | 5.3 | 0.5 |
|  | Ribose | 0.26 | n.d.[2] | 99.2 | 4.6 | 0.7 |
| *B. smithii* DSM 460 | Xylose | 0.38 | n.d.[2] | 99.3 | 4.3 | 1.0 |
|  | Arabinose | 0.24 | n.d.[2] | 99.2 | 5.3 | 0.6 |
|  | Ribose | 0.26 | n.d.[2] | 99.1 | 4.6 | 0.7 |

[1]Detection level is 0.05%.
[2]Not detectable.

TABLE 2

Acid production by thermophilic *Bacillus* species from pentose sugars in minimal medium at 54° C. after two transfers. Glucose was used as a control.

| Organism | C-source (3% w/w) | Lactic acid (% w/w) 48 h | Acetic acid[1] (% w/w) 48 h | Chiral purity L(+) lactate (S/R + S) * 100% 48 h | pH 48 h | OD 610 48 h |
|---|---|---|---|---|---|---|
| *B. coagulans* DSM 2314 | Xylose | 0.26 | n.d.[2] | 96.7 | 4.3 | 0.5 |
|  | Arabinose | 0.25 | n.d.[2] | 99.3 | 4.3 | 0.5 |
|  | Glucose | 0.23 | n.d.[2] | 99.4 | 5.1 | 0.4 |
| *B. smithii* DSM 2319 | Xylose | 0.21 | n.d.[2] | 98.1 | 6.0 | 0.2 |
|  | Arabinose | 0.20 | n.d.[2] | 99.5 | 6.0 | 0.3 |
|  | Glucose | 0.18 | n.d.[2] | 98.8 | 6.0 | 0.2 |

[1]Detection level is 0.05%.
[2]Not detectable.

EXAMPLE 2

Homolactic Fermentation of Xylose by B. coagulans DSM 2314

Materials and Methods

Strain, Medium and Fermentation Conditions

The microorganism used was *Bacillus coagulans* DSM 2314. The strain was maintained in glycerol stocks at −80° C. The bioreactor (3 L APPLIKON) contained 1.5 l of medium with the following composition: 2 g/l DAP, 3.5 g/l DAS, 10 g/l BIS-TRIS and 0.5 g/l KCl.

The bioreactor with medium was autoclaved at 121° C. (1.2 bar) for 20–30 min. Vitamins and trace element solutions were filter sterilized and added separately to the bioreactor after sterilization. Final concentrations of the growth factors were: 20 mg/l DL-methionine; 24 mg/l biotine, 12 mg/l thiamine, 15 mg/l $MgCl_2.2H_2O$, 0.1 g/l $CaCl_2$ and 1.5 ml of trace elements. Trace elements contained per 100 ml: 0.36 g of $FeCl_3$, 0.3 g of $MnCl_2$, 0.24 g of $CoCl_2$ and 0.12 of $ZnCl_2$. D-Xylose was added separately after sterilization to a final concentration of 50 g/l. The pH of the medium was adjusted to 6.5 with a concentrated solution of HCl. During the fermentation and due to the low biomass concentration achieved after 50 hours of fermentation, yeast extract was added to a final concentration of 10 g/l. The inoculum (~110 ml) was grown overnight at 50° C. in fermentation medium containing 1% D-Xylose. The inoculum was used after two transfers on xylose media.

The pH maintenance was achieved with automatic addition of KOH solution at 20% (w/v). The fermentation was performed at 54° C., pH 6.4 and agitation speed of 250–300 rpm. The temperature control was performed with the water bath LAUDA E100, while the pH reading/control data was performed by ADI 1020 BIO-PROCESSOR. All the data (pH and base consumption) was processed by the online data acquisition FM V5.0.

Samples were withdrawn before and after inoculation. During fermentation 5 to 30 ml samples were withdrawn periodically for OD measurement, Cell Dry Weight (CDW) measurement and analysis of L(+) and D(−) lactic acid, xylose and possible by-products (acetate). Samples were centrifuged (4–6° C., 6000–12000 rpm for 5–10 min) and the supernatant recovered/stored at −21° C. until further analysis.

Determination of Biomass Production

Dry matter was obtained through an initial weighted 0.45 μm MILLIPORE filter. A 15 to 20 ml sample was filtered, washed with 10 ml of demineralised water and dried at 105° C. for 1–2 days. The filter final weight allowed the measurement of the dried cells (CDW) in g/l.

Analysis of Sugars, Organic Acids and Ethanol

The residual xylose concentration of the samples was determined by the colorimetric assay using the Ferric-orcinol method as described by Chaplin, M. F., Kennedy, J. F. (1987). *Carbohydrate analysis: a practical approach.* IRL Press Limited (ISBN 0-947946-68-3)

(1). Xylose concentration as shown in Table 3 was analyzed with a DIONEX type DX 500 containing a CARBO-PAC PA-1 column and a PAD (Pulsed Amperometric Detection type ED 40) detector using a flow of 1.0 ml/min.

The L(+)lactate analysis of samples was performed by an enzymatic method which is an adapted version of Boehringer's GOD-PAP method for the quantification of glucose with glucose oxidase. L(+)lactic acid oxidase converts L(+)lactic acid into pyruvate and hydrogen peroxide. Hydrogen peroxide reacts in the presence of peroxidase with 4-aminophenazone and phenol to produce water-soluble red colored product that can be measured in a spectrophotometer at 540 nm.

Organic acids (lactic acid, acetic acid, formic acid, succinic acid) and ethanol as shown in Table 3 were measured using a derivatization and GLC. Optical purity of lactic acid was measured by GLC. D- and L-lactates were methylated to methyl-lactate and measured by headspace analysis on a chiral column.

Results

Strain *Bacillus coagulans* DSM 2314 was grown on 50 g/l xylose in minimal medium at 54° C. in a 3-liter fermentor (FIG. 1). During the fermentation, due to the low biomass concentration achieved after 50 hours of fermentation, yeast extract was added to a final concentration of 10 g/L. After circa 105 hours the xylose was depleted from the media and mainly converted to lactic acid (35 g/l) with only a low concentration of acetic acid (1 g/l) (Table 3). Optical purity of the lactic acid produced was 99%. Production of other organic acids were all below detection level.

The results indicate the ability of *B. coagulans* to perform a homofermentative lactic acid fermentation on pentose sugars. The maximum lactic acid production rate by *B. coagulans* in the non-optimized fermentation on xylose was 1.7 g/l/h as observed by the online data acquiring software.

TABLE 3

Organic acid production from 50 g/l xylose by *B. coagulans* DSM 2314.

| Time | Xylose g/l | Lactic acid g/l | Chiral purity (S/R + S) * 100% | Acetic acid g/l | Formic acid[1] g/l | Ethanol[1] g/l | Succinic acid[1] g/l |
|---|---|---|---|---|---|---|---|
| 100 h | 0.2 | 35 | 99 | 1 | <0.5 | <0.5 | <0.5 |

[1]Detection level is 0.5 g/l.

The invention claimed is:

1. A process for preparing lactic acid and/or lactate, comprising:

anaerobically fermenting in a fermentation broth a pentose-containing substrate by a moderately thermophilic *Bacillus* species selected from the group consisting of *Bacillus coagulans* and *Bacillus smithil* to form lactic acid and/or lactate; and recovering lactic acid and/or lactate from the fermentation broth;

wherein the fermenting is conducted at a temperature between 30° C. and 65° C.;

wherein the pentose-containing substrate comprises at least one of xylose, arabinose, and ribose; and wherein the pentose-containing substrate contains a smaller amount of hexose monomers than pentose monomers.

2. The process according to claim 1, wherein the pentose-containing substrate comprises xylose.

3. The process according to claim 1, wherein the pentose-containing substrate comprises arabinose.

4. The process according to claim 1, wherein the pentose-containing substrate comprises glucose.

5. The process according to claim 1, wherein the fermenting is performed by a mixture comprising *Bacillus coagulans* and another lactic acid-producing microorganism.

6. The process according to claim 1, wherein the fermenting is performed by a mixture comprising *Bacillus smithii* and another lactic acid-producing microorganism.

7. The process according to claim 1, wherein the moderately thermophilic *Bacillus* species is grown on a chemically defined medium.

8. The process according to claim 1, further comprising removing biomass from the fermentation broth prior to separating the lactic acid and/or lactate from the fermentation broth, wherein the moderately thermophilic *Bacillus* species selected from the group consisting of *Bacillus coagulans* and *Bacillus smithil* is grown on a chemically defined medium prior to the step of anaerobically fermenting.

9. The process according to claim 1, further comprising subjecting the lactic acid and/or lactate to one or more purification steps after separating the lactic acid and/or lactate from the fermentation broth, wherein the moderately thermophilic *Bacillus* species selected from the group consisting of *Bacillus coagulans* and *Bacillus smithii* is grown on a chemically defined medium prior to the step of homolactically and anaerobically fermenting.

\* \* \* \* \*